United States Patent [19]

Wass et al.

[11] Patent Number: 5,408,994
[45] Date of Patent: Apr. 25, 1995

[54] INHALATION DEVICE

[75] Inventors: Anthony C. L. Wass, Stamford; Brian R. Law, Western Park; Eric A. Baum, Loughborough; Peter D. Hodson, Trowell, all of Great Britain

[73] Assignee: Minnesota Mining and Manufacturing Company, St. Paul, Minn.

[21] Appl. No.: 50,440

[22] PCT Filed: Nov. 12, 1991

[86] PCT No.: PCT/GB91/01983
§ 371 Date: May 11, 1993
§ 102(e) Date: May 11, 1993

[87] PCT Pub. No.: WO92/08509
PCT Pub. Date: May 29, 1992

[30] Foreign Application Priority Data

Nov. 14, 1990 [GB] United Kingdom ............ 9024760

[51] Int. Cl.⁶ .................................... A61M 15/00
[52] U.S. Cl. ...................... 128/203.15; 128/200.14; 128/200.23
[58] Field of Search ............ 128/200.14, 200.23, 128/203.15, 203.21, 204.23, 204.26

[56] References Cited

U.S. PATENT DOCUMENTS

| | | | |
|---|---|---|---|
| 3,456,644 | 7/1969 | Thiel | 128/200.23 |
| 3,456,645 | 7/1969 | Brock | 128/200.23 |
| 3,565,070 | 2/1971 | Hanson | 128/173 |
| 3,598,294 | 8/1971 | Hedrick et al. | 222/402.2 |
| 3,789,843 | 2/1974 | Armstrong et al. | 128/173 |
| 4,664,107 | 5/1987 | Wass | 128/200.23 |
| 4,803,978 | 2/1989 | Johnson, IV et al. | 128/200.23 |
| 5,031,610 | 7/1991 | Armstrong et al. | 128/200.23 |
| 5,119,806 | 6/1992 | Palson et al. | 128/200.14 |

FOREIGN PATENT DOCUMENTS

| | | |
|---|---|---|
| 155964 | 4/1971 | New Zealand . |
| 159349 | 10/1971 | New Zealand . |
| 161990 | 12/1973 | New Zealand . |
| 90/13328 | 11/1990 | WIPO . |

*Primary Examiner*—Edgar S. Burr
*Assistant Examiner*—Aaron J. Lewis
*Attorney, Agent, or Firm*—Gary L. Griswold; Walter N. Kirn; Dale E. Hulse

[57] ABSTRACT

An inhalation device for administration of aerosolized medicament to the respiratory system of a patient comprising a housing defining a patient port and an air inlet, the housing containing means for dispensing a dose of aerosolized medicament, an inhalation-activatable triggering mechanism for initiating the dispensing means, and reset means. The triggering mechanism comprises a vane mounted for pivotable movement between closed and open positions, the vane being positioned within the patient port such that inhalation through the patient port generates an airflow from the air inlet to the patient port causing pivotable movement of the vane. The device further includes an activator component moveable between a restrained position and a dispensing position which movement causes dispensing of medicament from the dispensing means, the activator component being biased towards its dispensing position.

15 Claims, 10 Drawing Sheets

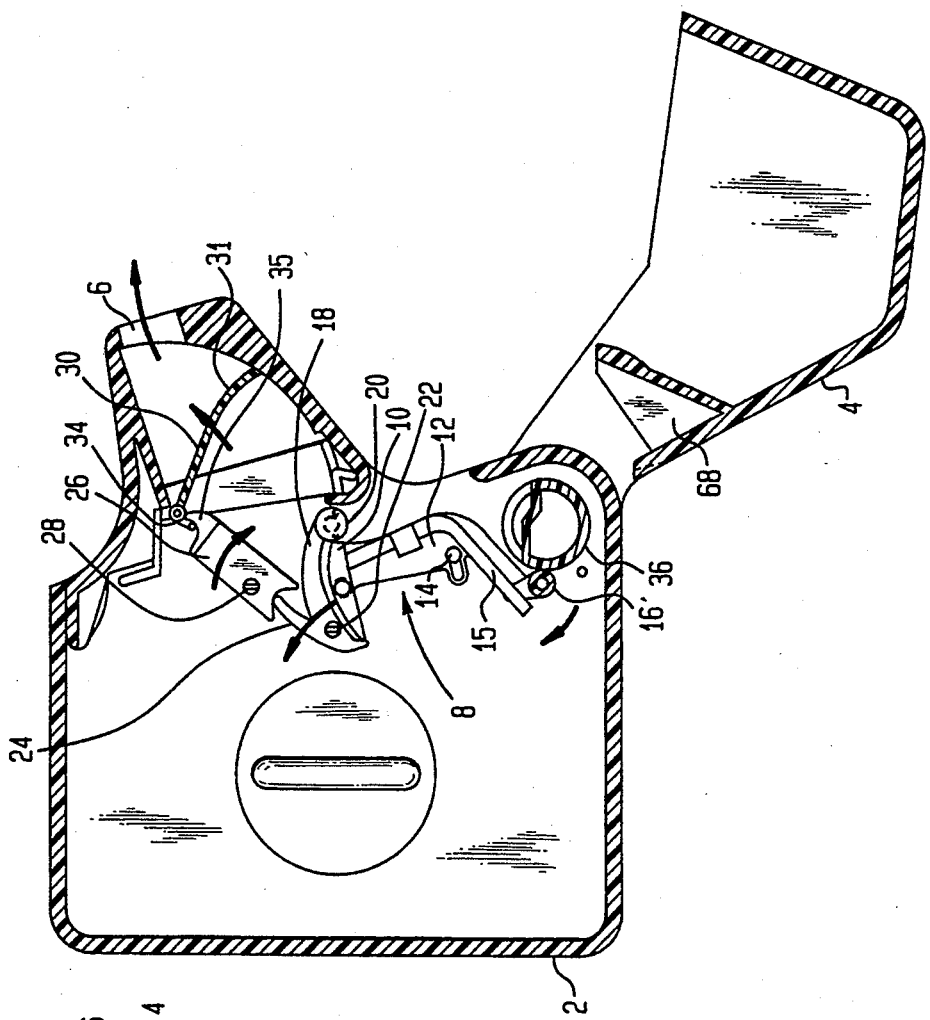
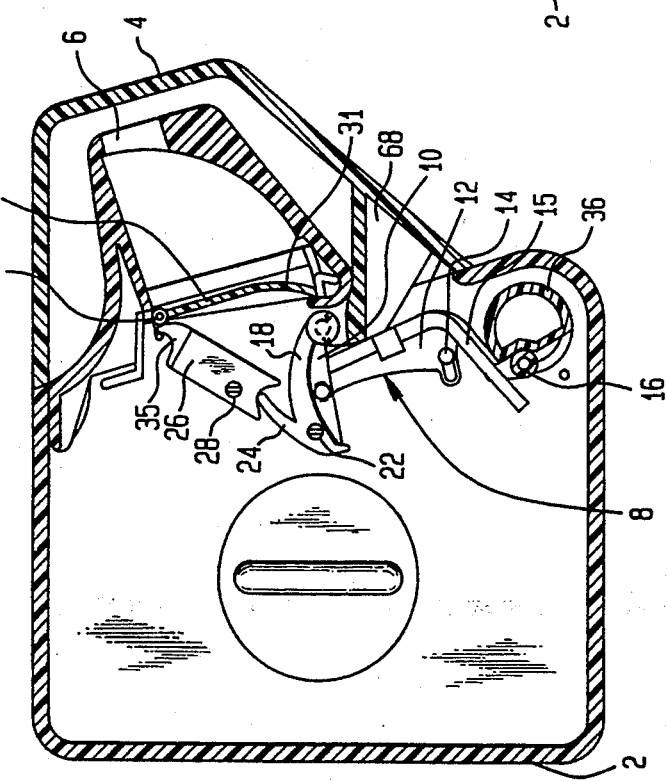

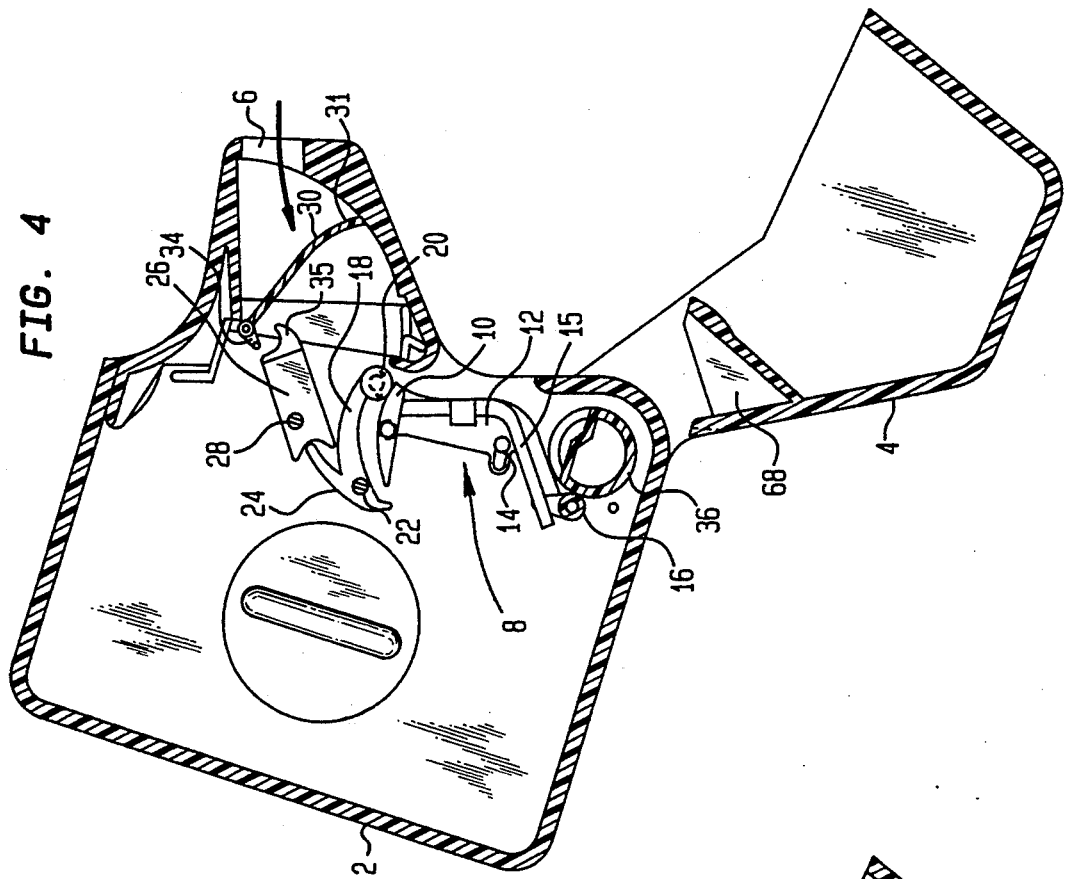
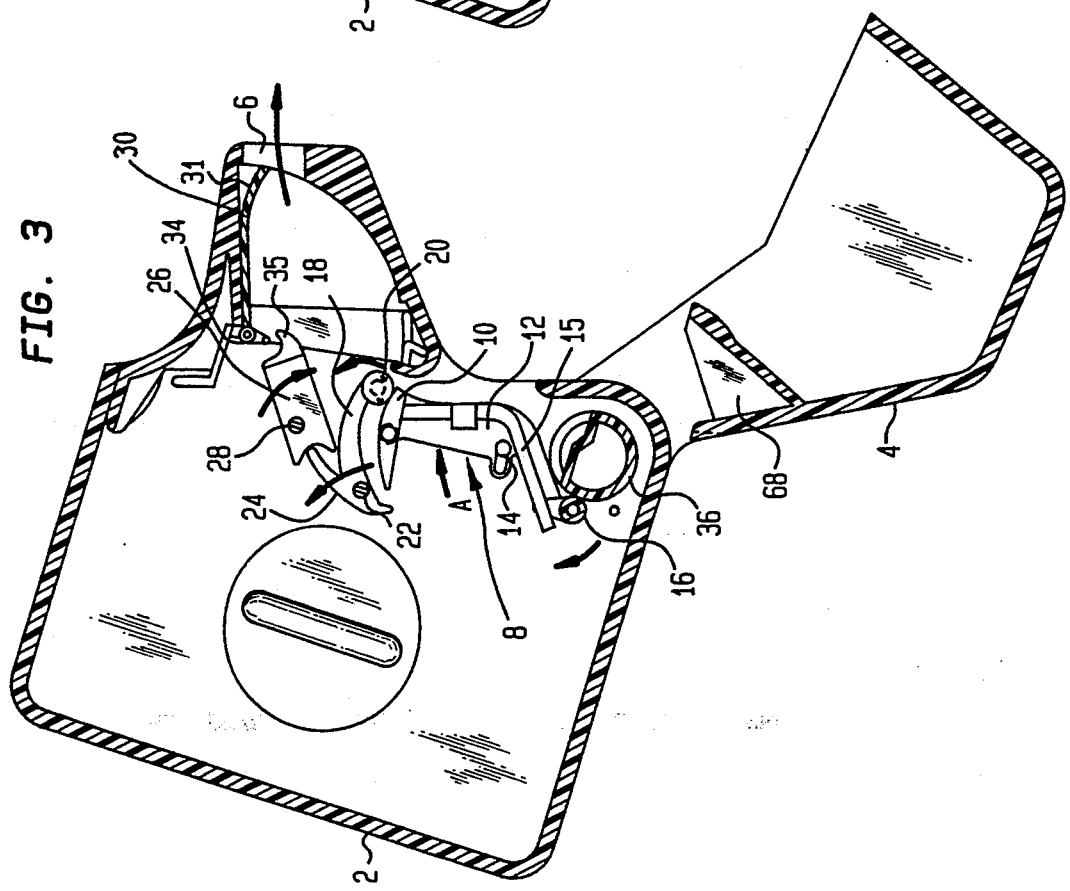

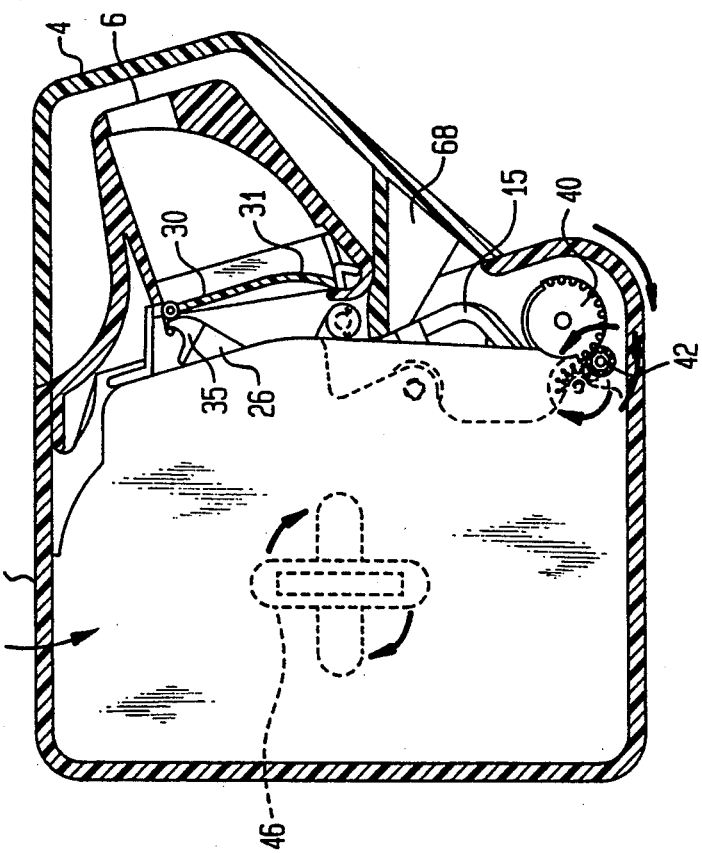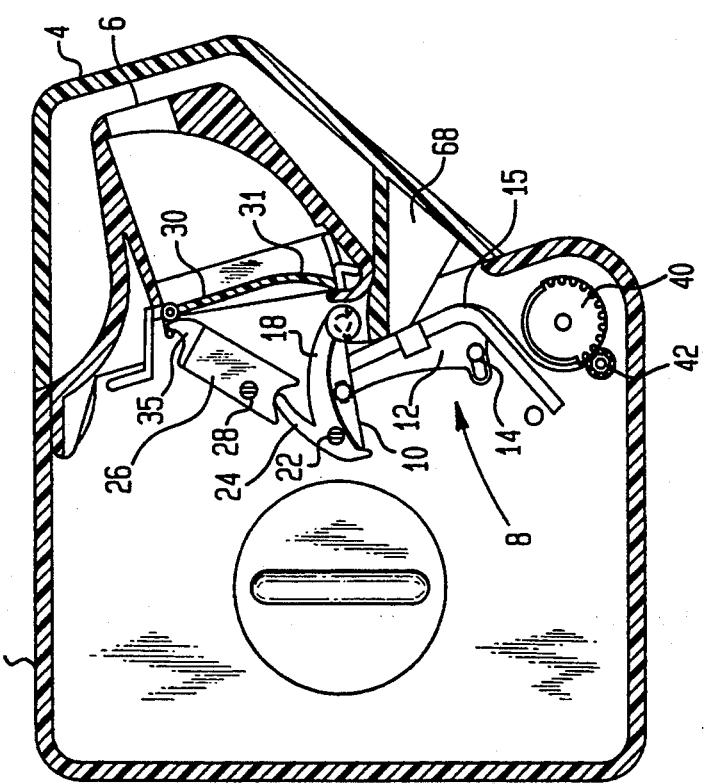

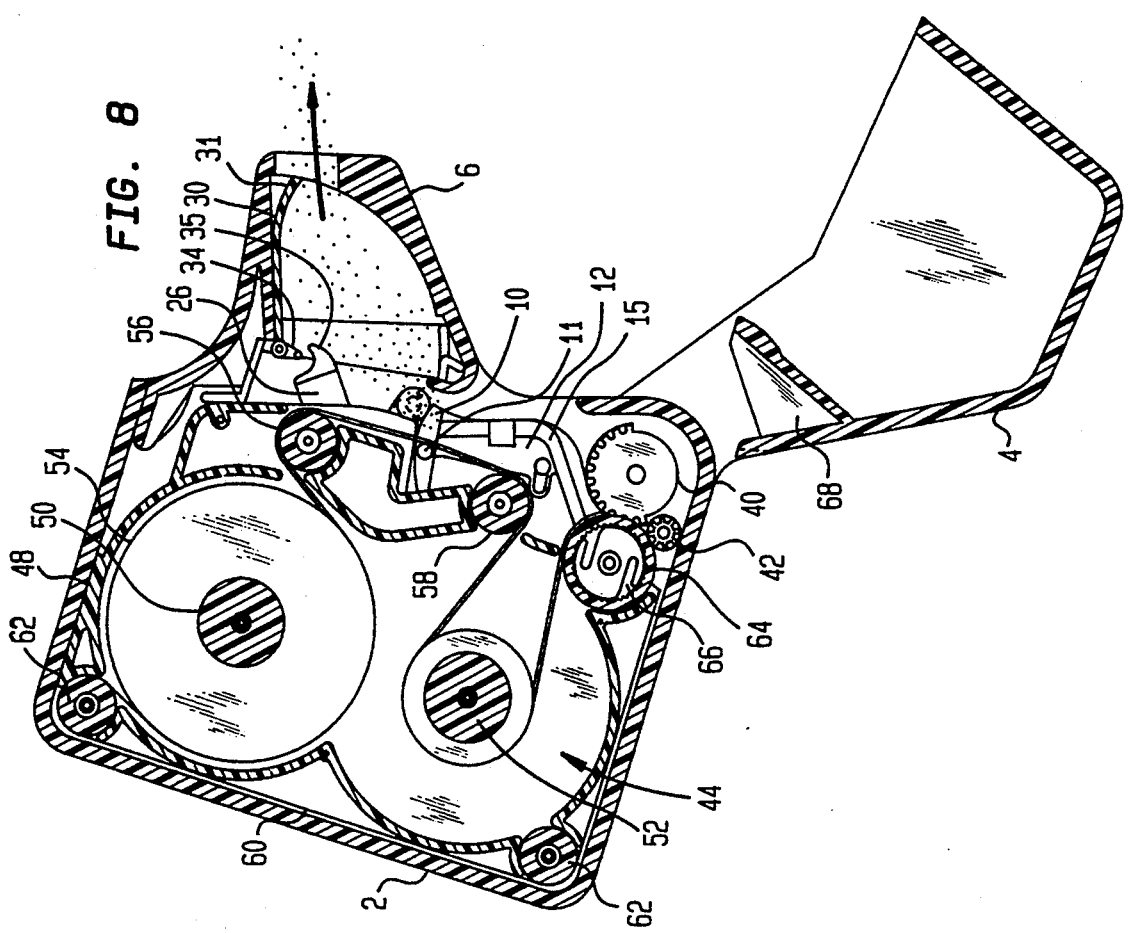
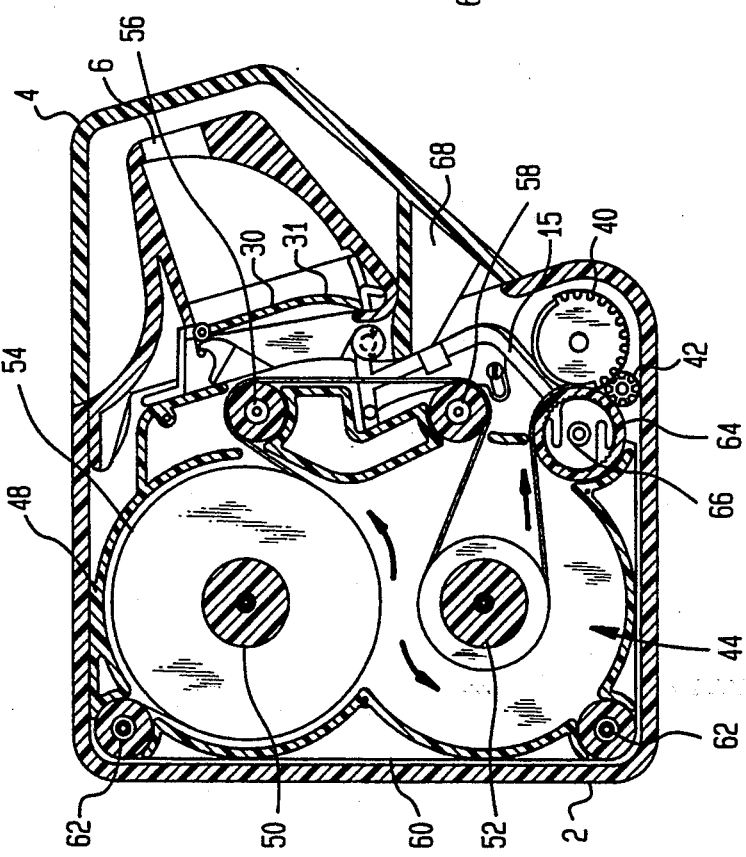

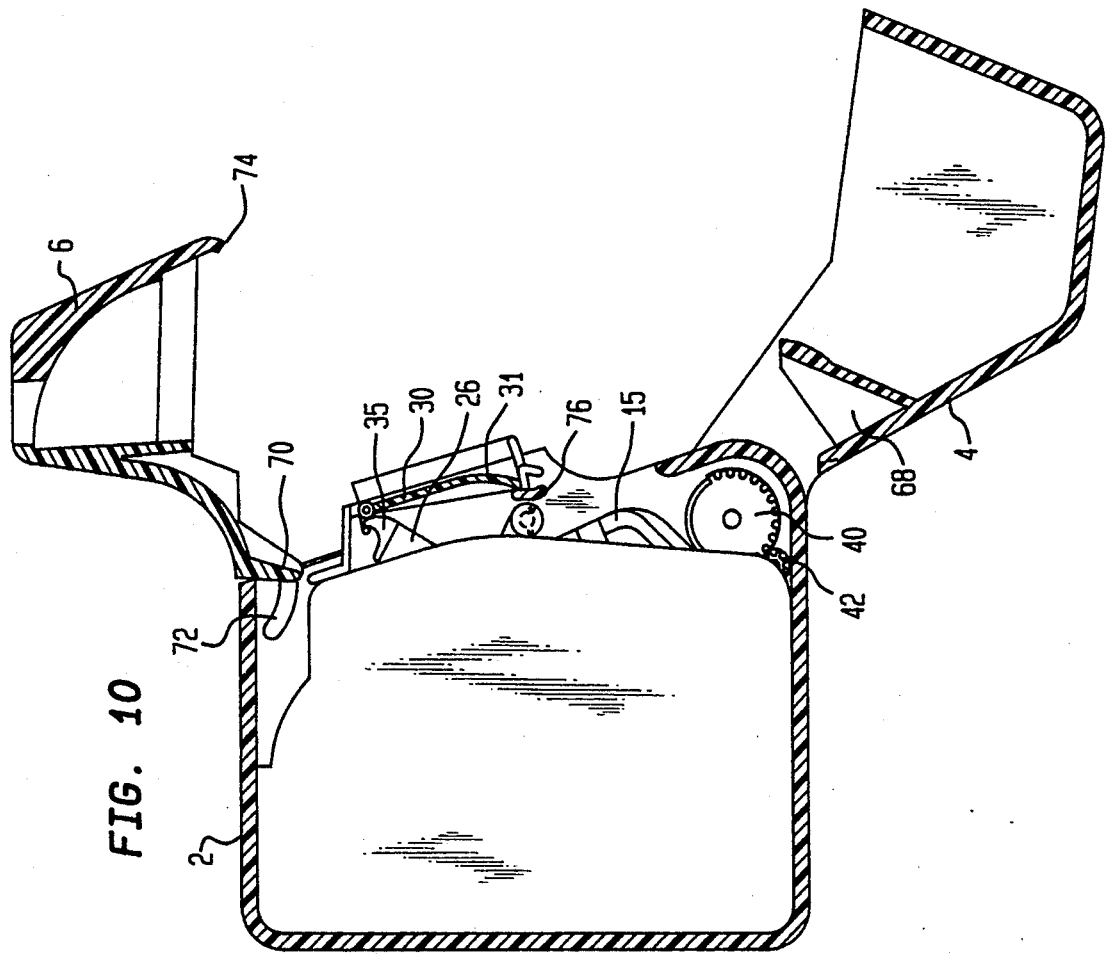

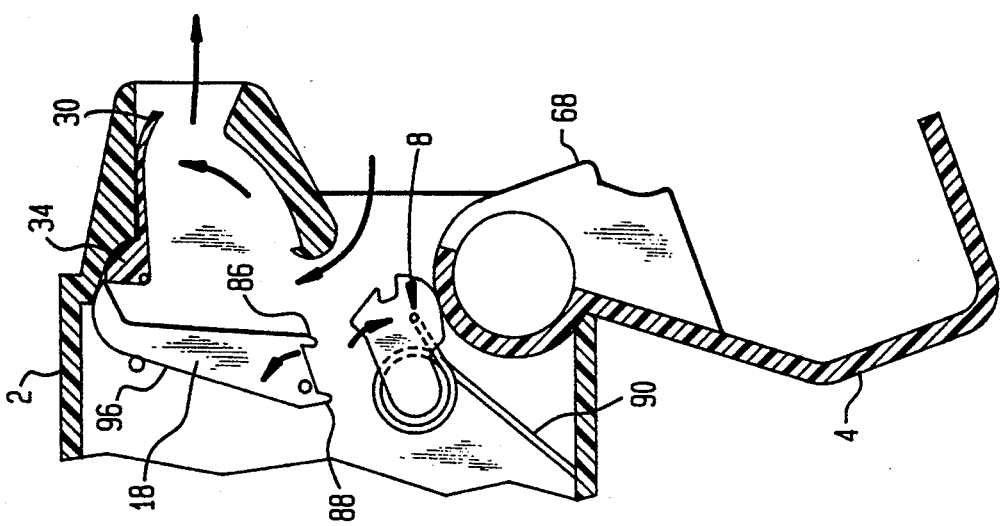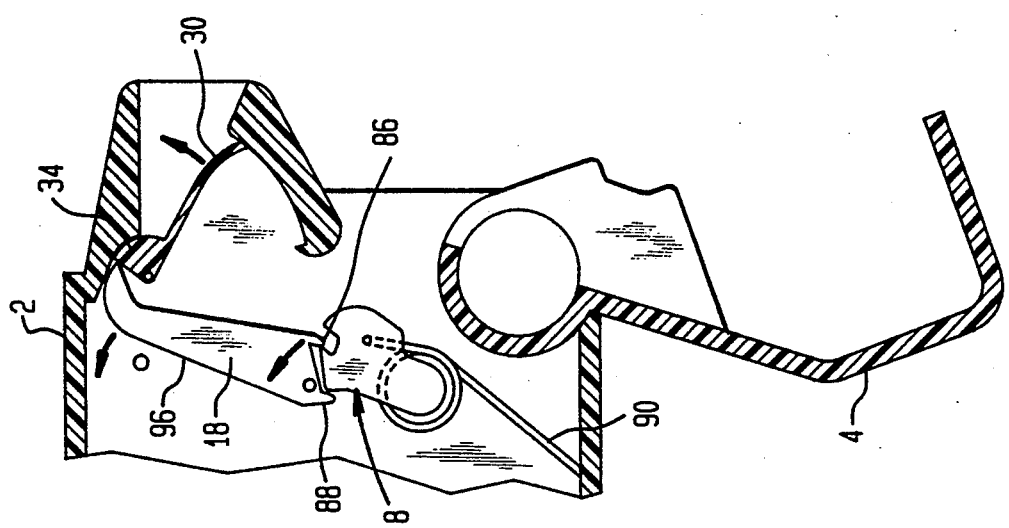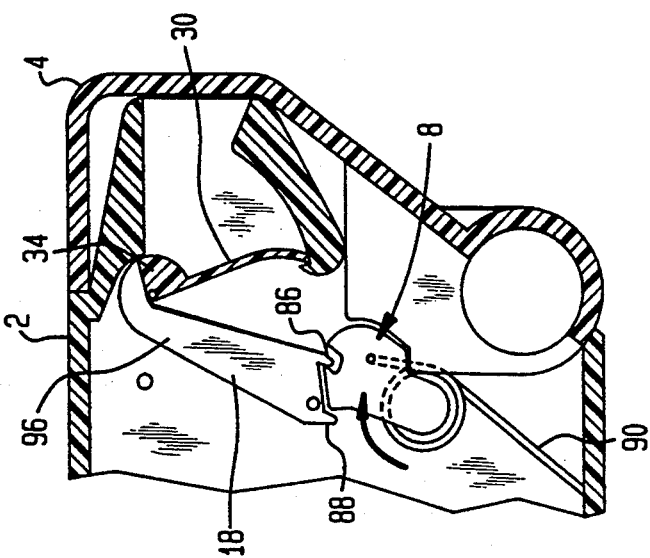

INHALATION DEVICE

FIELD OF THE INVENTION

This invention relates to inhalation activatable devices for the administration of medicaments for inhalation therapy.

BACKGROUND

Inhalation activatable dispensers for use with aerosol container assemblies are known, their general purpose being to afford proper co-ordination of the dispensing of a dose of medicament with the inhalation of the patient thereby allowing the maximum proportion of the dose of medicament to be drawn into the patient's bronchial passages. Examples of such dispensers are described in British Patent Specification Nos. 1,269,554, 1,335,378, 1,392,192 and 2,061,116 and U.S. Pat. Nos. 3,187,748, 3,456,644, 3,456,645, 3,456,646, 3,565,070, 3,598,294, 3,814,297, 3,605,738, 3,732,864, 3,636,949 and 3,789,843 and German Patent No. 3,040,641.

European Patent No. 147028 discloses an inhalation activatable dispenser for use with an aerosol container in which a latch mechanism releasing vane is pivotally mounted in an air passage between an aerosol outlet valve and a mouthpiece, which latch mechanism cannot be released if force to activate the dispenser is not applied before a patient inhales.

The dispenser generally comprises a housing having a mouthpiece and an air passage therethrough terminating at the mouthpiece, the housing being adapted to receive an aerosol container and having a support block with a socket adapted to receive the stem of the valve of the aerosol container and a through orifice communicating between the socket and the air passage, and latch means having parts movable between an engaged position in which movement of the container and the support block toward each other upon the application of a force to bias the container and the support block toward each other is prevented and a release position in which movement of the container and the support block toward each other in response to said force is permitted causing the stem to move to its inner discharge position, the latch means comprising a vane mounted on the housing in the air passageway between the orifice and the mouthpiece for movement toward the mouthpiece under the influence of inhalation through the mouthpiece to release the latch means in which the vane moves toward the mouthpiece from a blocking to a non-blocking position with respect to the passageway in response to inhaling at the mouthpiece and releases the latch means only during the application of said force to bias the container and support block toward each other.

Co-pending International Patent Application No. PCT/US90/02412 (Publication No. WO90/13328) discloses a dry powder inhalation device comprising a housing defining a chamber in communication with a patient port in the form of a mouthpiece or nasal adaptor, and an elongate carrier bearing a powdered medicament, the device being constructed and arranged such that areas of predetermined size of the elongate carrier may sequentially be exposed within the chamber, the device comprising one or more air inlets such that when a patient inhales through the patient port an air flow is established from the air inlet(s) to the patient port through the chamber such that particles of the powdered medicament of respirable size from said exposed area of the elongate carrier are entrained within the air flow.

The dry powder inhaler is capable of delivering multiple, uniform doses of a medicament to a patient. The device is simple to operate and does not require the patient to insert capsules of medicament or rely upon a separate reservoir of medicament in order to load the device for use. The medicament is generally preloaded on an elongate carrier, sections of which are sequentially exposed in the chamber for dispensing the medicament. The elongate carrier is preferably in the form of a tape having an array of depressions or microdimples holding micronised medicament and may be conveniently loaded on a spool (in a similar manner to a photographic film) or in a cassette (in a similar manner to an audio cassette). A preferred carrier is disclosed in European Patent Publication No. 0455463.

The device includes means for advancing the elongate carrier through the chamber to sequentially expose areas of the carrier for release of medicament during inhalation by the patient. The means for advancement may take a variety of forms depending upon the type of elongate carrier and whether the exposed areas of carrier are to be retained within the device. For example, tapes webs and belts may include a series of apertures which are engaged by one or more sprocketed guide wheels or rollers in a similar manner to a camera or printer. Alternatively, or in addition, the carrier may be wound on a take-up spool, rotation of the spool directly or via a drive belt causing the carrier to advance. The device may also include means for tensioning or otherwise maintaining the exposed area of the carrier within the chamber during inhalation by the patient.

The elongate carrier may be advanced into the chamber prior to inhalation by the patient or the carrier may be advanced into the aerosolisation chamber during inhalation to protect the powdered medicament from premature exposure.

In the preferred embodiment the elongate carrier is stored in a cassette both before and after exposure. The cassette may comprise one or preferably two spools together with idlers or other rollers and include an exposure frame positioned within the chamber, through which the carrier is advanced. The cassette may be removable to allow the device to be recharged with a new cassette. However, it is not essential for the exposed areas of the carrier to be retained within the device and spent carrier may be advanced to the exterior of the device through a slot in the housing whereupon disposal may be effected by the patient, optionally with the aid of a cutting edge. This arrangement is particularly suitable for a tape carrier which has transverse perforations to facilitate tearing off spent carrier.

The device preferably additionally comprises means for releasing medicament of respirable size from the exposed area of carrier independent of the patients' inspiratory effort. The medicament release means overcomes the binding of the medicament particles to the carrier by mechanical effort e.g. impaction, vibrations, gas flow etc. or electrostatically.

The means for releasing medicament from the carrier during inhalation is preferably triggered in response to the patient inhaling in order to avoid the patient having to synchronise inhalation and actuation of the release mechanism. Airflow detection may conveniently be accomplished by means of a movable vane positioned within the chamber or patient port, motion of the vane causing actuation of the release mechanism. Such a vane may also be constructed to prevent a patient exhaling through the device and/or to prevent exhaled air from reaching the stored carrier thereby avoiding any problems associated with moisture.

SUMMARY OF THE INVENTION

The present invention provides an improved triggering mechanism which is suitable for use in such an inhalation device and may also be employed in other dry powder or pressurised aerosol inhalation devices.

According to the present invention there is provided an inhalation device for administration of aerosolised medicament to the respiratory system of a patient comprising a housing defining a patient port in the form of a mouthpiece or nasal adaptor and an air inlet, the housing containing means for dispensing a dose of aerosolised medicament, an inhalation-activatable triggering mechanism for initiating the dispensing means, and reset means, in which the triggering mechanism comprises a vane mounted for pivotal movement between closed and open positions, the vane being positioned such that inhalation through the patient port generates an air flow from the air inlet to the patient port causing pivotal movement of the vane, and an activator component movable between a restrained position and a dispensing position which movement causes dispensing of medicament from the dispensing means, the activator component being biased towards its dispensing position, the triggering mechanism being constructed and arranged such that:

a) when the activator component is in the restrained position and the vane is in the closed position the activator component is held in its restrained position by mechanical blocking action of the vane either directly by the vane or via one or more movable intermediate components whose movements to release the mechanical blocking action are controlled by the vane, b) pivotal movement of the vane from its closed to its open position removes said mechanical blocking action allowing movement of the activator component to its dispensing position and c) operation of the reset means causes movement of the activator component from its dispensing to its restrained position which movement causes, directly or indirectly via one or more intermediate components, the vane to move from its open or a partially open position to its closed position if the vane is not closed.

Preferably, the activator component is arranged to move pivotally between its restrained position and its dispensing position, but it may alternatively be arranged to move reciprocally, linearly or in some other fashion.

The invention provides a triggering mechanism for actuating an inhaler device which obviates the need for handling co-ordination by the patient and actuates at low flow-rates, e.g., 30 liters per minute, within the capabilities of most asthma sufferers. The components of the triggering mechanism are arranged such that they may mechanically interengage during the reset cycle thus by simply returning the activator component to its restrained position it is positively ensured that the other components are returned to their respective positions ready for the next triggering sequence. This arrangement ensures the mechanism will be reset regardless of the orientation of the inhaler device during the reset procedure since it does not rely on gravity to return any of the components to the required position. Furthermore, since the various components interengage during the reset cycle there are no problems associated with synchronisation of different moving parts of the mechanism.

The vane is conveniently positioned within the patient port of the inhalation device and may be arranged such that it may be wholly or partially returned from its open to its closed position prior to the reset cycle providing it is then positively engaged by a component of the triggering mechanism as the mechanism is reset. This freedom of movement of the vane, which may take place under the influence of gravity should the patient's inhalation falter or which may take place should the patient exhale through the patient port, allows the mouthpiece to be closed by the vane preventing contaminants entering the housing prior to resetting the triggering mechanism. The vane pivot point is ordinarily positioned towards one end of the vane.

The triggering mechanism is particularly suitable for use in the inhalation devices of International Publication Nos. WO90/13327 and WO90/13328. However, the triggering mechanism may readily be employed in other dry powder and pressurised aerosol devices which utilise a biased activator component.

In its simplest form the triggering mechanism may simply comprise a vane and activator component. In such an arrangement the vane comprises blocking and reset surfaces positioned at an end of the vane near the pivot point, e.g. by providing a pair of projections or arms on the vane, such that:

a) when the activator component is in the restrained position and the vane is in the closed position the blocking surface mechanically engages the activator component preventing movement of the activator component from its restrained position.

b) when the vane is pivoted from its closed to open position the blocking surface is moved out of mechanical engagement with the activator component allowing it to move from the restrained to the dispensing position and c) operation of the reset means to move the activator component from its dispensing to its restrained position causes engagement of the reset surface by the activator component pivoting the vane to its closed position thereby mechanically blocking the activator component in its restrained position.

It is not always convenient to position the activator component close to the vane in some inhalation devices and it may be convenient to employ one or more intermediate components between the vane and activator to allow separation thereof.

For example, a three component triggering mechanism may comprise a vane, catch and activator component, the catch being pivotally mounted for movement between a blocking position in which it mechanically blocks movement of the activator component from its restrained position and a release position in which it allows movement of the activator component to its dispensing position, the catch and vane each having a respective engagable end which allows movement transfer therebetween, the catch having a second end having a blocking surface which engages the activator component in its restrained position and a reset surface which is engaged by the activator component during movement from its dispensing to its restrained position under the influence of the reset means thereby causing movement of the catch to its blocking position and vane to its closed position.

A four component triggering mechanism may comprise a vane, rocker, catch and activator component, the catch being pivotally mounted for movement between a blocking position in which it mechanically blocks movement of the activator component from its restrained position and a release position in which it allows movement of the activator component to its dispensing position, the rocker being mounted for pivotal movement and having one end engagable with one end of the vane to allow movement transfer therebetween and a second end engagable with the catch to allow movement transfer therebetween, the catch having a blocking surface which engages the activator component in its restrained position and a reset surface which is engaged by the activator component during movement from its dispensing to its restrained position under the influence of the reset means thereby causing movement of the catch to its blocking position, and movement of the rocker and thereby movement of the vane to its closed position.

Whilst the use of three or four component triggering mechanisms may impart additional friction into the system at the pivot points and contacting surfaces, the friction may readily be overcome by positioning the pivot points to gain a mechanical advantage on the lever principle. The use of such a multi-component triggering mechanism also readily allows the triggering mechanism to be fitted into available areas in the inhalation device since it does not require the presence of a long straight lever, and the pivot points of the components need not be arranged linearly.

The reset means for the triggering mechanism preferably acts directly on the activator component and moves it against its biasing means back to its restrained position. The reset means may conveniently take the form of a projection on a hinged cover for the mouthpiece such that the inhalation device is reset when the cover is closed after the patient has used the device.

BRIEF DESCRIPTION OF THE DRAWINGS

The invention will now be described with reference to the accompanying drawings in which:

FIGS. 1 to 10 represent a cross-section through an inhaler in accordance with the invention illustrating the various stages of operation.

Figure 11:
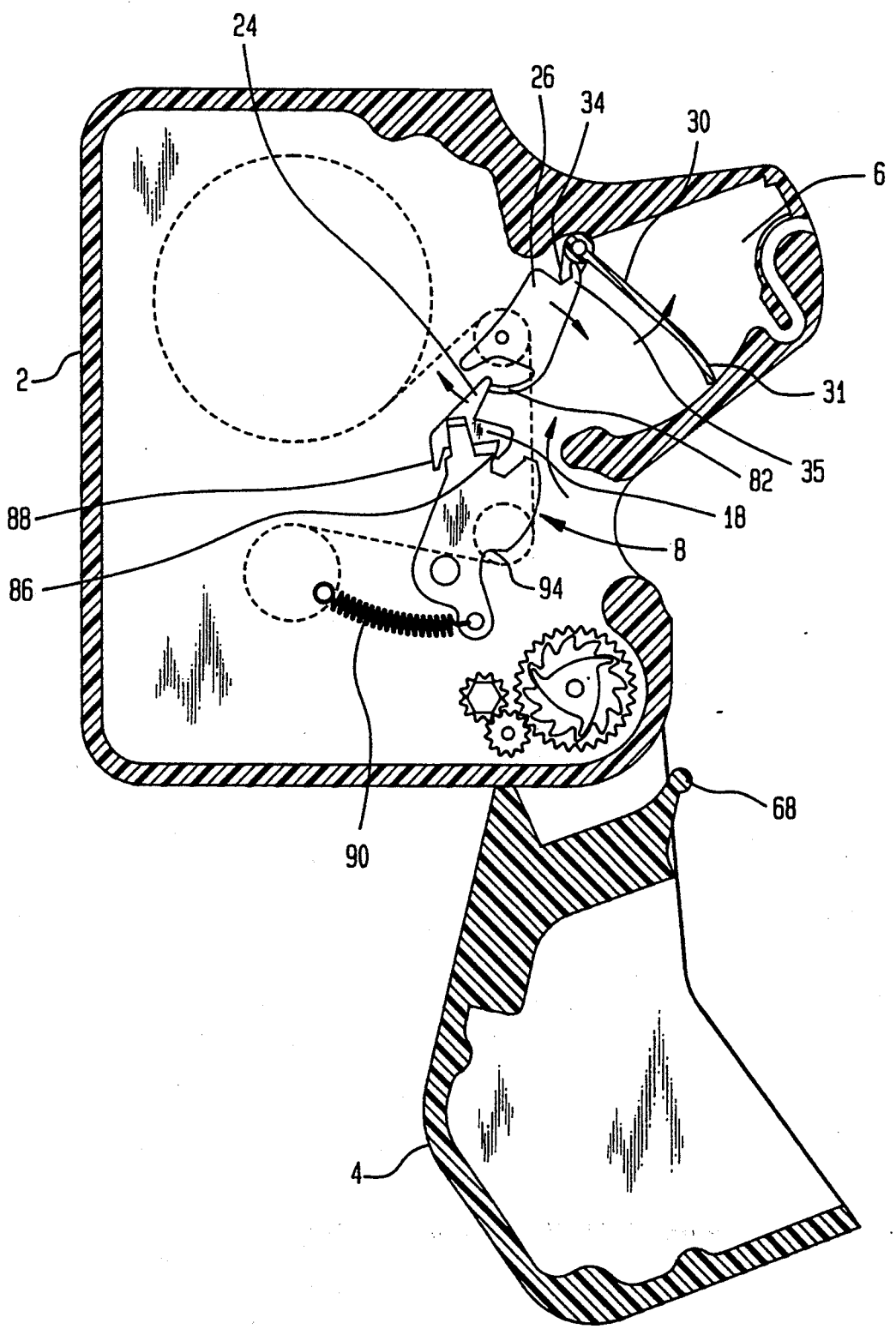
FIGS. 11 and 12 represent cross-sections through a second inhaler in accordance with the invention, FIGS. 13 (a) to 13 (c) represent diagrams of a further triggering mechanism for use in the invention.

The inhaler of FIGS. 1 to 10 is of a type disclosed in International Publication No. WO90/13328, the medicament being carried on a tape contained within a removable cassette.

In FIGS. 1 to 10 like numerals represent like parts.

FIGS. 1 to 5 of the accompanying drawings illustrate a section through an inhaler with the cassette removed. The inhaler comprises a housing (2), a movable cover (4) and a patient port (6) in the form of a mouthpiece.

DETAILED DESCRIPTION

The means for releasing medicament is in the form of an activator generally shown at (8) which comprises an impactor head (10) for striking the elongate carrier, the impactor head being attached to a stem (12) which is mounted for movement and rotation about point (14). An impactor spring (15) provides a bias to move the activator to its dispensing position and is secured to the stem (12) and has a roller (16) at one end thereof. The activator is held in a restrained position by a catch (18) which has a blocking surface (20) in the form of a roller engaging the impactor head (10) of the activator. The catch (18) is mounted for pivotal movement about point (22) and has an arm (24) engaged by rocker (26). The rocker (26) is mounted for pivotal movement about point (28). The means for detecting patient inspiration comprises a vane (30) positioned within the mouthpiece (6). The vane (30) is mounted for pivotal movement about point (32) and includes a projection (34) which engages the surface (35) of the rocker (26).

FIG. 1 shows the device with the cover closed and the components restrained. Opening of the cover (FIG. 2) causes pivotal movement of cam (36) acting on roller (16) thereby imparting tension to the impactor spring (15). Movement of the impactor head (10) is prevented by the catch (18). When the patient inhales through the mouthpiece the vane (30) pivots as shown in the direction of the arrow. Pivotal movement of the vane (30) in turn causes pivotal movement of the rocker (26) and pivotal movement of the catch (18) as shown in the direction of the arrows, causing the roller (20) to lift clear of the impactor head (10) thereby allowing the activator to move in the direction of the arrow (A) (FIG. 3) and the impactor head (10) to strike the elongate carrier.

The vane (30) is lifted to the top of the passage of the mouthpiece during inhalation. The end of the vane (30) includes a curved portion (31) which extends in to the potential pathway for exhaled air, thereby ensuring the vane (30) will snap shut immediately, should the patient exhale through the mouthpiece (6) (FIG. 4). Alternatively, the vane may be straight, but a curve (not shown) in the roof of the mouthpiece may ensure that the end of the vane extends into the potential pathway for exhaled air.

FIG. 5 illustrates drive gear (40) which is connected to the cover (4) for rotation during opening of the cover (4). The drive gear (40) drives idler gear (42).

Referring to FIG. 6, the cassette generally shown at (44), containing the elongate carrier, is inserted in the device and may be retained by a pivoted catch (46). The cassette (44) comprises a housing (48) (FIG. 7) and contains spools (50 and 52), the elongate carrier (54) being Wound on spool (50) and extending via rollers (56 and 58) to spool (52). A drive belt (60) passes round idler rollers (62) and contacts the carrier (54) on spool (50), throughout its entire length around the rollers (56 and 58) and on spool (52). The drive belt also extends around driven roller (64).

When the cover (4) is opened the gear train (40) is rotated causing rotation of idler gear (42) and driven roller (64), thereby causing movement of the drive belt and advancement of the tape (54). The driven roller (64) includes a non-return ratchet generally shown at (66) and also includes a similar drive ratchet (not shown) mounted lower on the shaft.

FIG. 8 illustrates the inhaler during inhalation through the mouthpiece. The impactor head (10) comprises a raised impactor surface (11) which strikes the drive belt (60) which is in contact with the tape (54) thereby imparting sufficient energy to the tape (54) to release the powdered medicament in to the air stream formed by the patient's inhalation.

FIG. 9 illustrates the movement of the various components during the reset cycle which is achieved by closing of the cover. The activator (8) is moved to its restrained position by reset projection (68) mounted on the inside of the cover. As the activator (8) is returned towards its restrained position by the reset projection (68) it engages the reset surface (78) of the catch (18) causing pivotal movement of the catch (18) in the direction of the arrows. The arm (24) of the catch (18) engages the rocker (26) causing pivotal movement of the rocker (26) in the direction of the arrows. Movement of the rocker (26) causes engagement between the surface (35) and the projection (34) on the vane (30). The point during the reset cycle at which this engagement will occur depends upon the position of the vane when the reset cycle is commenced. If the vane is in its opened position the rocker will immediately engage the vane but if the vane is in the closed position, e.g. if the patient has exhaled through the mouthpiece, engagement of the rocker and vane will not occur until the end of the reset cycle. Engagement will occur part way through the reset cycle if the vane is in an intermediate position.

The mouthpiece (6) may be integrally formed with the housing or may be removable for cleaning purposes. FIG. 10 of the drawings illustrates a removable mouthpiece (6). The mouthpiece comprises a peg (70) which is engaged within slot (72) in the housing of the inhaler. The peg (70) may be disengaged from the slot for complete removal of the mouthpiece (6). The mouthpiece (6) additionally comprises a retaining clip (74) which engages with the sides of aperture (76) formed on the housing of the inhaler.

Figure 12:
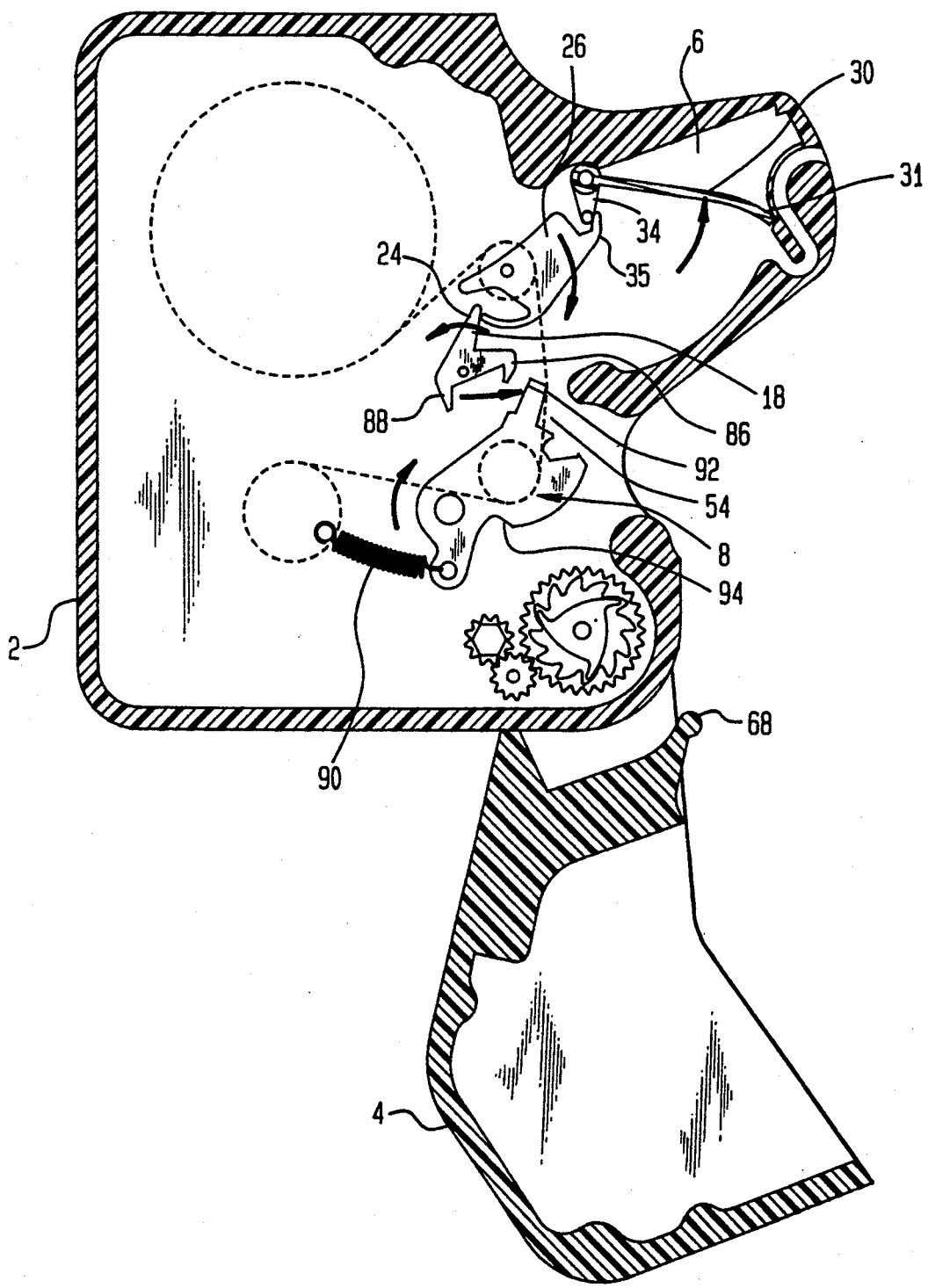

FIGS. 11 and 12 illustrate an inhaler similar to that of FIGS. 1 to 10 having a modified triggering mechanism. Like numerals in these Figures represent like components in FIGS. 1 to 10.

The rocker (26) comprises an arm (82) which engages the arm (24) of the catch (18) during the triggering and reset cycles. The catch comprises a blocking arm (86) which engages the activator (8) in its restrained position and reset arm (88) which engages the activator (8) during the reset cycle. The activator (8) is biased towards its dispensing position by spring (90).

FIG. 11 shows the inhaler at the onset of inhalation through the mouthpiece (6) with the vane (30) lifting causing pivotal movement of the rocker (26) and catch (18) in the direction of the arrows.

FIG. 12 shows the inhaler dispensing the medicament; the vane (30) has lifted to its open position causing sufficient movement of the rocker (26) and catch (18) such that the blocking arm (86) of the catch (18) disengages the activator (8) allowing the activator (8) to pivot to its dispensing position under the influence of spring (90). The impactor head (92) carried on the activator (8) strikes the elongate carrier to dispense powdered medicament into the airflow for inhalation by the patient.

When the cover is closed, reset projection (68) pushes the activator (8) back to its restrained position thereby tensioning spring (90). During the reset cycle the activator engages reset arm (88) of the catch (18) causing pivotal movement of the catch (18). The arm (24) of the catch (18) engages arm (82) of the rocker (26) causing pivotal movement of the rocker (26). Surface (35) of the rocker engages projection (34) of the vane (30) to complete vane closure thereby resetting the triggering mechanism. Upon complete closure of the cover (4) the reset projection preferably moves out of contact with the activator (8) and is positioned within recess (94) formed in the activator (8) to ensure that the activator (8) is restrained by the catch (18) with no strain on the cover (4). This arrangement also allows the cover (4) to be fully closed.

In the inhalation devices illustrated by FIGS. 1 to 12, the rocker (26) is arranged such that it is unable to rotate so far clockwise as to no longer be engagable by the catch (18) and such that the surface (35) of the rocker (26) extends sufficiently to ensure that the projection (34) of the vane (30) is always engagable.

FIGS. 13(a) to (c) represent an inhaler similar to those disclosed in. FIGS. 1 to 12 in which the triggering mechanism comprises a vane (30), catch (18) and activator (8). The rocker of the previous triggering mechanisms is omitted and the catch (18) comprises a long arm (96) which engages the projection (34) on the vane (30). As inhalation commences (FIG. 13(b)) the vane (30) lifts causing the catch (18) to pivot in the direction of the arrows. When the vane (30) lifts to its open position (FIG. 13(c)) the catch (18) disengages the activator (8) causing it to move to its dispensing position under the torque provided by spring (90). The triggering mechanism is reset by closing the cover (4), reset project, on (68) moving the activator (8) back to its restrained position, the activator engaging reset arm (88) on the catch (18), which in turn engages the projection (34) on the vane (30) with arm (96), thereby completing the reset cycle.

Figure 14A:
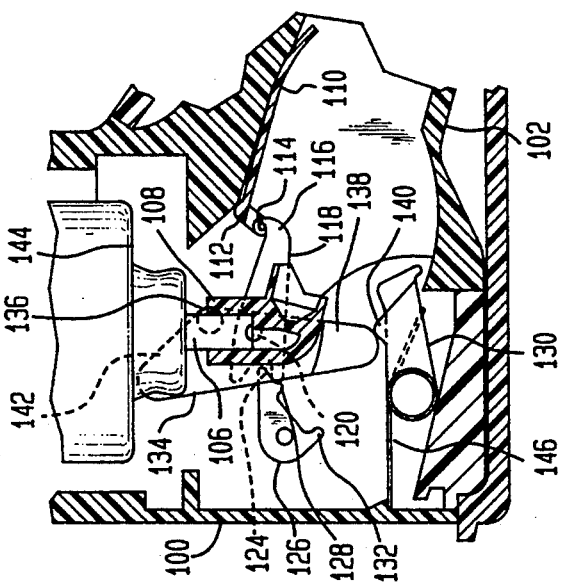
FIGS. 14(a) to 14(c) represent partial cross-sections of an inhaler in accordance with the invention having a pressurised aerosol container, and FIGS. 15 (a) and 15 (h) represent diagrams of the triggering and reset cycles of a two component triggering mechanism.

FIG. 14 illustrates the application of the triggering assembly of the invention to a pressurised aerosol inhaler of the type disclosed in European Patent No. 147028 and commercially available under the registered trade marks AEROLIN AUTOHALER. FIG. 14 shows the dispensing end of the inhaler comprising a housing (100) having a mouthpiece (102) and containing a pressurised aerosol container equipped with a metering valve, generally shown at (104). The valve stem (106) is retained within a nozzle block (108). The valve is actuated to dispense a metered dose of medicament by moving the valve stem (106) inwardly relative to the container.

The triggering mechanism comprises a vane (110) pivotally mounted at (112) having a projection (114) which engages arm (116) on rocker (118). The rocker (118) is pivotally mounted at (120) and has a projection (122) engaging arm (124) of catch (126). Catch (126) comprises a blocking arm (128) which engages activator (130) and a reset arm (132). A blocking lever (134) is pivotally mounted at (136) and has one end (138) which engages shoulder (140) of the activator (130) and a second end (142) which abuts the valve ferrule (144). The activator (130) is provided with a reset spring (146).

Figure 14B:
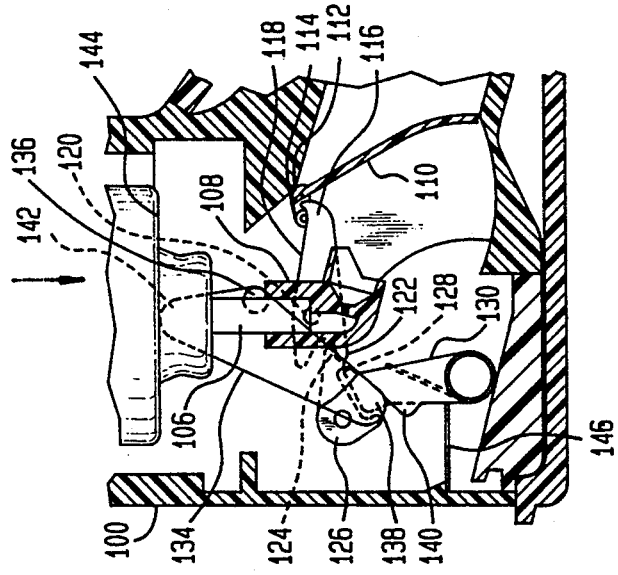

In use a priming force is applied to the aerosol container in the direction of the arrow in FIG. 14(b), for example by pushing a lever (not shown) on the top of the inhaler which acts to compress a spring against the base of the aerosol container.

Figure 14C:
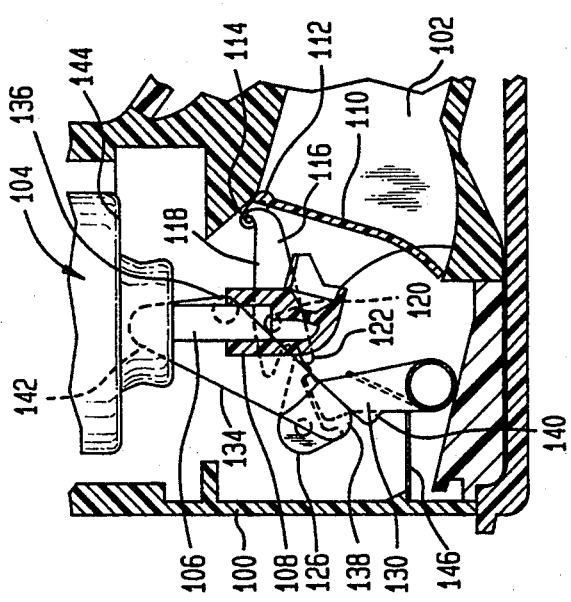

The priming force exceeds the force on the return spring (146) and movement of the aerosol container is prevented by the blocking lever (134) abutting the valve ferrule, movement of the blocking lever (134) being prevented by the restrained activator (130). The activator (130) is thus biased towards its dispensing position under the influence of that part of the priming force which reaches the activator (130) via the blocking lever (134), which part force exceeds the opposing force from the return spring (146). As the patient begins to inhale through the mouthpiece (102) (FIG. 14(b)) the vane (110) starts to lift causing pivotal movement of the rocker (118) and catch (126) in the direction of the arrows. When the vane (110) is fully open the movement transferred via the rocker (118) to the catch (126) is sufficient to disengage the catch (126) from the activator. The priming force transmitted through the aerosol container, valve ferrule and blocking lever (134) to the activator (130) is sufficient for the activator (130) to pivot as shown in FIG. 14(c) which allows pivotal movement of the blocking lever (134) thereby enabling downward movement of the aerosol container firing the valve to dispense a dose of medicament. When the dose has been administered the priming force is removed and the aerosol container is raised under the influence of the internal spring in the valve (not shown). The reset spring (146) causes the activator (130) to pivot towards its restrained position which movement of the activator causes pivotal movement of the blocking lever to its blocking position. The movement of the activator (130) is transferred to the catch (126) and thence to the rocker (118) and thence to the vane (110) to complete the reset cycle in a similar manner to the triggering mechanism illustrated in FIGS. 11 and 12.

FIGS. 15(a) to 15(h) illustrate the triggering and reset sequences of a two component triggering mechanism comprising a vane (150) and activator (154). The vane (150) is pivoted at (152) and the activator is pivoted at (156) and is biased in the clockwise direction. When the vane (150) is closed the activator (154) is held in its restrained position by the blocking action of projection (158) near the end of the vane (150). As the vane (150) is pivoted under the influence of airflow, the projection (158) disengages the activator (154) allowing it to move to its dispensing position.

Figure 15A:
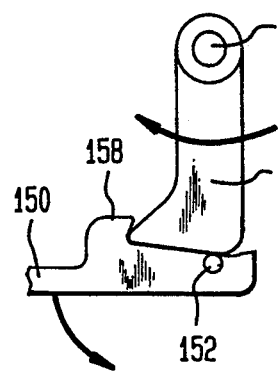
Figure 15B:
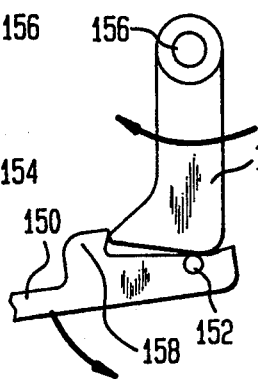
Figure 15C:
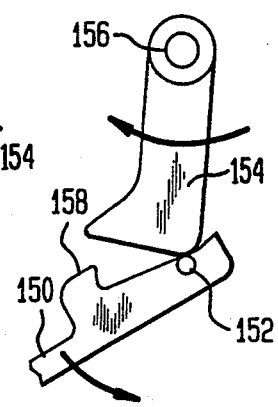
Figure 15D:
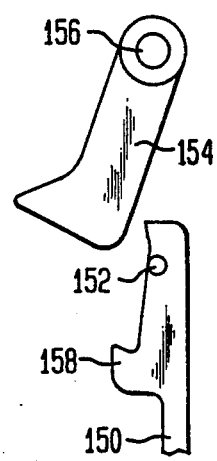
Figure 15E:
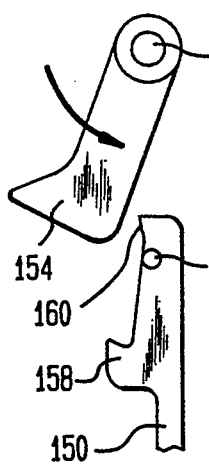
Figure 15F:
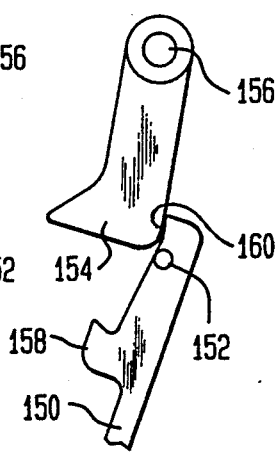
Figure 15G:
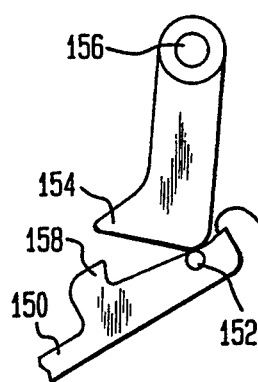
Figure 15H:
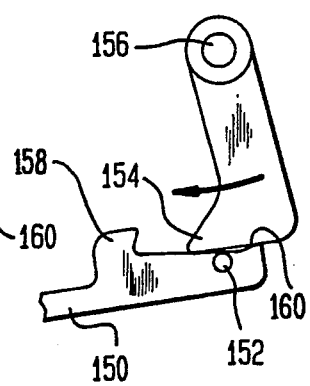

During the reset cycle (FIG. 15(b)) the activator (154) is urged to its restrained position causing it to engage a reset surface (160) on the end of the vane (150) pivoting the vane to its closed position thereby retaining the activator in its restrained position.

We claim:

1. An inhalation device for administration of aerosolised medicament to the respiratory system of a patient comprising a housing defining a patient port in the form of a mouthpiece or nasal adaptor and an air inlet, the housing containing means for dispensing a dose of aerosolised medicament, an inhalation-activatable triggering mechanism for initiating the dispensing means, and reset means, in which the triggering mechanism comprises a vane mounted for pivotal movement between closed and open positions, the vane being positioned within the patient port such that inhalation through the patient port generates an air flow from the air inlet to the patient port causing pivotal movement of the vane to its open position, and an activator component movable between a restrained position and a dispensing position which movement causes dispensing of medicament from the dispensing means, the activator component being biased towards its dispensing position, the triggering mechanism being constructed and arranged such that:

a) when the activator component is in the restrained position and the vane is in the closed position the activator component is held in its restrained position by mechanical blocking action of the vane either directly by the vane or via one or more movable intermediate components whose movements to release the mechanical blocking action are controlled by the vane, b) pivotal movement of the vane from its closed to its open position removes said mechanical blocking action allowing movement of the activator component to its dispensing position and c) operation of the reset means causes movement of the activator component from its dispensing to its restrained position which movement causes, directly or indirectly via one or more intermediate components, the vane to move from its open or a partially open position to its closed position if the vane is not closed.

2. An inhalation device as claimed in claim 1 in which the vane comprises blocking and reset surfaces positioned at an end of the vane towards the pivot point such that:

a) when the activator component is in the restrained position and the vane is in the closed position the blocking surface mechanically engages the activator component preventing movement of the activator component from its restrained position.

b) when the vane is pivoted from its closed to open position the blocking surface is moved out of mechanical engagement with the activator component allowing it to move from the restrained to dispensing position and c) operation of the reset means to move the activator component from its dispensing to restrained position causes engagement of the reset surface by the activator component pivoting the vane to its closed position thereby mechanically blocking the activator component in its restrained position.

3. An inhalation device as claimed in claim 1 in which the triggering mechanism comprises the vane, a catch and the activator component, the catch being pivotally mounted for movement between a blocking position in which it mechanically blocks movement of the activator component from its restrained position and a release position in which it allows movement of the activator component to its dispensing position, the catch and vane each having a respective engagable end which allows movement transfer therebetween, the catch having a second end having a blocking surface which engages the activator component in its restrained position and a reset surface which is engaged by the activator component during movement from its dispensing to its restrained position under the influence of the reset means thereby causing movement of the catch to its blocking position and vane to its closed position.

4. An inhalation device as claimed in claim 1 in which the triggering mechanism comprises the vane, a rocker, a catch and the activator component, the catch being pivotally mounted for movement between a blocking position in which it mechanically blocks movement of the activator component from its restrained position and a release position in which it allows movement of the activator component to its dispensing position, the rocker being mounted for pivotal movement, the rocker having one end engagable with one end of the vane to allow movement transfer therebetween and a second end engagable with the catch to allow movement transfer therebetween, the catch having a blocking surface which engages the activator component in its restrained position and a reset surface which is engaged by the activator component during movement from its dispensing to restrained position under the influence of the reset means thereby causing movement of the catch to its blocking position, and movement of the rocker and thereby movement of the vane to its closed position.

5. An inhalation device as claimed claim 1 in which the vane is free to pivot from its open to closed position without operation of the reset means.

6. An inhalation device claimed in claim 1 additionally comprising a cover for said patient port movable between open and closed positions, such that closure of the cover causes movement of the activator component from its dispensing to its restrained position.

7. An inhalation device as claimed in claim 1 comprising a reservoir of medicament in the form of a dry powder.

8. An inhalation device as claimed in claim 7 in which the dry powder is carried on an elongate carrier and the dispensing means comprises means to strike a portion of the elongate carrier to dislodge dry powder from the elongate carrier when the activator component moves to its dispensing position.

9. An inhalation device as claimed in claim 8 in which the elongate carrier is wound on a spool, hub or reel within a cassette and the inhalation device comprises means to advance the carrier to sequentially expose areas for dispensing medicament therefrom.

10. An inhalation device as claimed in claims 1 which comprises a pressurised aerosol container equipped with a metered dose dispensing valve.

11. An inhalation device as claimed in claim 10 which comprises means to apply a priming force to the dispensing valve and in which the triggering mechanism exerts a blocking action preventing actuation of the dispensing valve, the blocking action being removed when the activator component moves to its dispensing position.

12. An inhalation device as claimed in claim 1 further comprising means for moving the vane to its closed position upon exhalation through the patient port so as to substantially close off said patient port and substantially prevent the entry of exhaled air into the inhalation device through the patient port.

13. An inhalation device as claimed in claim 12 wherein said means for moving the vane to its closed position upon exhalation through the patient port comprises a curved surface formed on the end of the vane.

14. An inhalation device as claimed in claim 12 wherein said means for moving the vane to its closed position upon exhalation through the patient port comprises a curved surface formed in the roof of the patient port.

15. An inhalation device as claimed in claim 6 wherein said reset means comprises a projection formed on said cover, said projection contacting said actuator component and moving said actuator component to its restrained position as said cover is moved to its closed position.

* * * * *

UNITED STATES PATENT AND TRADEMARK OFFICE
CERTIFICATE OF CORRECTION

PATENT NO.: 5,408,994
DATED: April 25, 1995
INVENTOR(S): Anthony C. L. Wass et al.

It is certified that error appears in the above-identified patent and that said Letters Patent is hereby corrected as shown below:

Col. 5, line 53, "and" should be --to--.

Col. 8, line 26, "project, on" should be --projection--.

Col. 11, line 5, claim 5, line 1, after "claimed" insert --in--.

Col. 11, line 8, claim 6, line 1, after "device" insert --as--.

Col. 11, line 27, claim 10, line 1, "claims" should be --claim--.

Signed and Sealed this

Seventh Day of November, 1995

Attest:

BRUCE LEHMAN

Attesting Officer

Commissioner of Patents and Trademarks